United States Patent
Tani et al.

(10) Patent No.: US 9,907,549 B2
(45) Date of Patent: Mar. 6, 2018

(54) TISSUE SUTURING DEVICE

(71) Applicants: Tohru Tani, Otsu (JP); Shigeyuki Naka, Otsu (JP)

(72) Inventors: Tohru Tani, Otsu (JP); Shigeyuki Naka, Otsu (JP)

(73) Assignee: National University Corp. Shiga University of Medical Science, Otsu-Shi, Shiga (JP)

( * ) Notice: Subject to any disclaimer, the term of this patent is extended or adjusted under 35 U.S.C. 154(b) by 316 days.

(21) Appl. No.: 14/365,620

(22) PCT Filed: Dec. 14, 2012

(86) PCT No.: PCT/JP2012/082583
§ 371 (c)(1),
(2) Date: Jun. 14, 2014

(87) PCT Pub. No.: WO2013/089257
PCT Pub. Date: Jun. 20, 2013

(65) Prior Publication Data
US 2014/0358165 A1 Dec. 4, 2014

(30) Foreign Application Priority Data
Dec. 14, 2011 (JP) .................................. 2011-273043

(51) Int. Cl.
*A61B 17/04* (2006.01)
*A61B 18/18* (2006.01)
*A61B 18/00* (2006.01)

(52) U.S. Cl.
CPC ...... *A61B 17/0469* (2013.01); *A61B 18/1815* (2013.01); *A61B 2018/0063* (2013.01);
(Continued)

(58) Field of Classification Search
CPC ...... A61B 18/1815; A61B 2018/00589; A61B 2018/00619; A61B 2018/0063; A61B 2018/1823; A61B 2018/1869
See application file for complete search history.

(56) References Cited

U.S. PATENT DOCUMENTS 6,162,220 A  12/2000  Nezhat
6,887,240 B1 *  5/2005  Lands ............... A61B 17/29
                                                606/207

(Continued)

FOREIGN PATENT DOCUMENTS

EP       2233098 A1     9/2010
JP    2005-312807 A    11/2005
(Continued)

OTHER PUBLICATIONS

A machine translated Office Action dated Sep. 6, 2016, for the corresponding Japanese Patent Application.
(Continued)

*Primary Examiner* — Gregory Anderson
(74) *Attorney, Agent, or Firm* — Don D. Cha; Hamilton DeSanctis & Cha, LLP (57) ABSTRACT

Provided is a surgical instrument that is substitutable for an operation of placing each stitch with a threaded needle or a stapler. It is confirmed that, in a tissue suturing device including a clamping section, and a protruding section including a central conductor and/or an external conductor for applying a microwave, the protruding section and the clamping section bring fragmentary portions of tissues to be sutured into contact or overlap with each other, and coagulate and/or fix contact or overlap portions with the microwave, to thereby stitch the tissues to be sutured.

12 Claims, 8 Drawing Sheets

(52) U.S. Cl.
CPC ............... *A61B 2018/00482* (2013.01); *A61B 2018/00494* (2013.01); *A61B 2018/00589* (2013.01); *A61B 2018/00619* (2013.01); *A61B 2018/1823* (2013.01); *A61B 2018/1869* (2013.01)

(56) References Cited

U.S. PATENT DOCUMENTS

| | | |
|---|---|---|
| 9,314,295 B2 * | 4/2016 | Garrison ............ A61B 18/1442 |
| 2002/0177848 A1 | 11/2002 | Truckai |
| 2007/0054539 A1 | 3/2007 | Wakikaido |
| 2010/0024976 A1 | 9/2010 | Nau |
| 2010/0249769 A1 | 9/2010 | Nau, Jr. et al. |

FOREIGN PATENT DOCUMENTS

| | | |
|---|---|---|
| JP | 2011-056288 A | 3/2011 |
| WO | 2003/068046 A2 | 8/2003 |

OTHER PUBLICATIONS

A machine translated First Office Action dated Nov. 2, 2015, for the corresponding Chinese Patent Application.
A machine translated Second Office Action dated Jul. 12, 2016, for the corresponding Chinese Patent Application.
First Office Action dated Jun. 6, 2016, for the corresponding European Patent Application.

* cited by examiner

TISSUE SUTURING DEVICE

TECHNICAL FIELD

The present invention relates to a surgical instrument, and more specifically, to a tissue suturing device (stitch) for joining tissue edges with microwaves to coagulate and fix tissues instead of suturing the tissue edges with a surgical stitch, thereby attaining substantially the same effect for the tissues to be sutured as in the case of suturing the tissues with a surgical stitch.

This application claims priority from Japanese Patent Application No. 2011-273043, the disclosure of which is incorporated herein by reference.

BACKGROUND ART

Devices for assisting a surgical operation with microwaves have been developed, and devices for coagulation, cutting, peeling, puncture, and sealing have been developed into a practical level by the inventors of the present invention. For example, a microwave coagulation puncture needle and a microwave sealing device are known. However, it is only a stapler that is a surgical instrument capable of eliminating, when suturing tissues of mesentery or the like, the need for an operation of placing each stitch with a threaded needle to fix the tissues. Therefore, the surgeon who performs suturing requires a long period of operation time or sophisticated skill, and further, foreign matters such as a surgical stitch or a stapler remain in the surgical region.

A document regarding a suturing device using microwaves (see Patent Literature 1) has been reported. However, the structure of this suturing device is completely different from that of the tissue suturing device according to the present invention. Further, the suturing device disclosed in the above-mentioned document has a complex structure, and hence it is difficult to put this suturing device into practical use as a simple device. Besides, in endoscopic surgery, gastrointestinal walls need to be stitched, but it is impossible to perform the operation through an endoscope.

In this context, there has been demanded a development of a surgical instrument that is substitutable for the suturing (adhering) of tissues through stitching of the tissues with a surgical stitch or a stapler.

CITATION LIST

Patent Literature

[PTL 1] JP 11-47144 A

SUMMARY OF INVENTION

Technical Problems

The present invention has been made to solve the problems described above, and therefore provides a development of a surgical instrument that is substitutable for an operation of stitching tissues with a threaded needle or a stapler.

Solution to Problems

The inventors of the present invention have earnestly studied so as to solve the problems described above, and as a result, confirmed that, in a tissue suturing device including a clamping section, and a protruding section including a central conductor and/or an external conductor for applying a microwave, the protruding section and the clamping section bring fragmentary portions of tissues to be sutured into contact or overlap with each other, push the tissues into cavities under pressure, respectively, and coagulate and/or fix the pushed contact or overlap portions with the microwave, thereby being capable of suturing the tissues to be sutured. Thus, the present invention has been attained.

More specifically, the two opposing protruding sections are pressed against the tissues with a shift therebetween so that one protruding section pushes the tissues and another protruding section further pushes the tissues from the opposite side in the same manner. Accordingly, the fragmentary portions of the tissues to be sutured are brought into contact or overlap with each other, and the contact or overlap portions are coagulated and/or fixed with the microwave, thereby being capable of suturing the tissues to be sutured.

Note that, the tissues after removal of the protruding sections pressed thereagainst are coagulated and fixed, and simultaneously with adhesion of the tissues under pressure, the tissue is connected to the opposite tissue so that the fixation and support are intensified. Thus, the suturing is completed substantially in the same manner as in the case of suturing the tissues with a surgical stitch (see FIGS. 2C and 3b).

That is, the present invention includes the following Items.

"1. A tissue suturing device, including:

a clamping section; and a protruding section including a central conductor and/or an external conductor for applying a microwave, the protruding section and the clamping section being configured to bring fragmentary portions of tissues to be sutured into contact or overlap with each other, and coagulate and/or fix contact or overlap portions with the microwave, to thereby stitch the tissues to be sutured.

2. The tissue suturing device according to Item 1, in which the clamping section includes two or more opposing clamping sections, in which the protruding section includes protruding sections fixed to the two or more opposing clamping sections, the protruding sections including one or more central conductors and/or one or more external conductors for applying the microwave, and in which the two or more opposing clamping sections and the opposing protruding sections are configured to bring the fragmentary portions of the tissues to be sutured into contact or overlap with each other, and coagulate and/or fix the contact or overlap portions with the microwave, to thereby stitch the tissues to be sutured.

3. A tissue suturing device according to Item 1 or 2, in which the clamping sections have cavity, in which the cavity serve as receptacle for the protruding sections fixed to the two or more opposing clamping sections, and in which the opposing protruding sections and the cavities of the two or more opposing clamping sections are configured to bring the fragmentary portions of the tissues to be sutured into contact or overlap with each other, and coagulate and/or fix the contact or overlap portions with the microwave, to thereby stitch the tissues to be sutured.

4. A tissue suturing device according to Item 3, in which the opposing protruding sections and the cavities of the two or more opposing clamping sections are configured to bring the fragmentary portions of the tissues to be sutured into contact or overlap with each other, push the tissues into the cavities under pressure, respectively, and coagulate and/or fix the contact or overlap portions with the microwave, to thereby stitch the tissues to be sutured.

5. A tissue suturing device according to any one of Items 2 to 4, in which the tissue suturing device has a structure with a shape of scissor tongs, in which the two or more opposing clamping sections are fixed to respective cutting edges of the scissor tongs, and in which, when grips of the scissor tongs are grasped, the opposing protruding sections, the two or more opposing clamping sections, and/or the cavities of the two or more opposing clamping sections are configured to bring the fragmentary portions of the tissues to be sutured into contact or overlap with each other, and coagulate and/or fix the contact or overlap portions with the microwave, to thereby stitch the tissues to be sutured.

6. A tissue suturing device according to any one of Items 3 to 5, in which the protruding sections include two or more protruding sections formed in an array, and in which the cavities include two or more cavities formed in an array so as to serve as receptacles for the opposing protruding sections formed in the array.

7. A tissue suturing device according to Item 6, in which the array includes a plurality of arrays.

8. A tissue suturing device according to any one of Items 3 to 5, in which the protruding sections include linear protruding sections, and in which the cavities have a structure to serve as receptacles for the linear protruding sections.

9. A tissue suturing device according to any one of Items 1 to 6, in which the protruding section includes the central conductor, and in which the clamping section includes the external conductor.

10. A tissue suturing device according to any one of Items 1 to 6, in which the protruding sections and the cavities include two sets of protruding sections and cavities that are opposed to each other, in which one of the protruding sections includes the central conductor, and in which another of the protruding sections includes the external conductor.

11. A tissue suturing device according to any one of Items 1 to 10, in which a diameter of the protruding section, the central conductor, and/or the external conductor is decreased gradually or stepwise toward a tip end thereof.

12. A tissue suturing device according to any one of Items 1 to 10, in which the protruding section has a halved structure."

Advantageous Effects of Invention

During the surgical operation, the gap between the tissues needs to be closed through a simple operation. For example, in a case where edges of mesentery are to be sutured after a small intestine is ablated, the gap needs to be closed by placing several stitches of the surgical stitch in the vicinity of the margins. However, a device substituting for the suturing through connection of membranous objects has not yet been provided thus far.

In the tissue suturing device according to the present invention, the operation corresponding to ligation and suturing with a surgical stitch is completed substantially in no time. When this operation is performed several times, the closure of a long ligament can easily be completed within a short period of time. Further, when the surgeon feels that the stitched region is weak during the suturing of an intestinal tract or the like, the microwave is applied to only the marginal region of the weak region, thereby being capable of attaining the same effect as in the operation corresponding to placement of the surgical stitch and addition of one stitch.

In the tissue suturing device according to the present invention, which includes the clamping sections having a large number of protruding sections fixed on flat surfaces thereof, an operation of pinching tissues having two flat surfaces and applying the microwave is repeated, thereby being capable of coagulating and/or fixing linear or planar tissues to each other.

BRIEF DESCRIPTION OF DRAWINGS

FIG. 2A corresponds to a top view and a side view of the clamping section 1 being a base-like object.

FIG. 2C is a view illustrating an example of use of the tissue suturing device according to the present invention. The two protruding sections 6 push tissues into the opposing clamping sections 1, respectively. Note that, the protruding section 6 may have a halved structure and a tapered structure instead of a shape for a puncture needle.

FIG. 2D is a view illustrating an example of use of the tissue suturing device according to the present invention. Cutting edges are arranged on the protruding sections 6 of the clamping sections 1 being a base-like object. The cutting edges are not opposed to the clamping sections being a base-like object, but both the cutting edges are opposed to each other through intermediation of tissues or the like. Microwaves are applied from the tip end portions of the cutting edges to compress and coagulate the tissues.

FIG. 3a is a view illustrating coagulation treatment that is performed by aligning incision lines, grabbing and clamping tissues, and applying microwaves. FIG. 3b is a view illustrating that adhesion is maintained through coagulation operations performed three times even under tension applied to the incision.

see FIG. 5a) protruding section 6 is provided. FIG. 4 illustrates that the microwaves can be applied sufficiently to the vicinity of regions to be sutured.

DESCRIPTION OF EMBODIMENTS

Now, embodiments of the present invention are described with reference to the attached drawings. However, those drawings are examples that symbolically illustrate the contents of the present invention, and the present invention is not limited to those embodiments.

The mechanism of the present invention includes two or more opposing clamping sections 1, protruding sections 6 fixed to the respective clamping sections and including one or more central conductors 2 and/or external conductors 9 for applying microwaves, and cavities 3 serving as receptacles for the protruding sections fixed to the opposing clamping sections. Therefore, when the opposing clamping sections 1 are joined to each other, tissues can be adhered under pressure until the flat surfaces are brought into contact with each other (FIG. 1).

More specifically, each of two surfaces of different tissues pinched between the opposing clamping sections is pushed into the opposite tissue, and microwaves are applied to the tissues so that the tissues are coagulated.

Further, in principle, the microwaves are propagated from the central conductor toward the external conductor 9, and hence the tissue suturing device according to the present invention requires the central conductor and the external conductor 9. For example, when the protruding section 6 includes both of the central conductor 2 and the external conductor 9, the microwaves can be applied to fragmentary portions of tissues to be sutured. Further, when the protruding section 6 includes only the central conductor 2, it is only necessary that another protruding section 6 or the clamping section 1 include the external conductor 9. Still further, when the protruding section 6 includes only the external conductor 9, it is only necessary that another protruding section 6 or the clamping section 1 include the central conductor 2.

Figure 1:
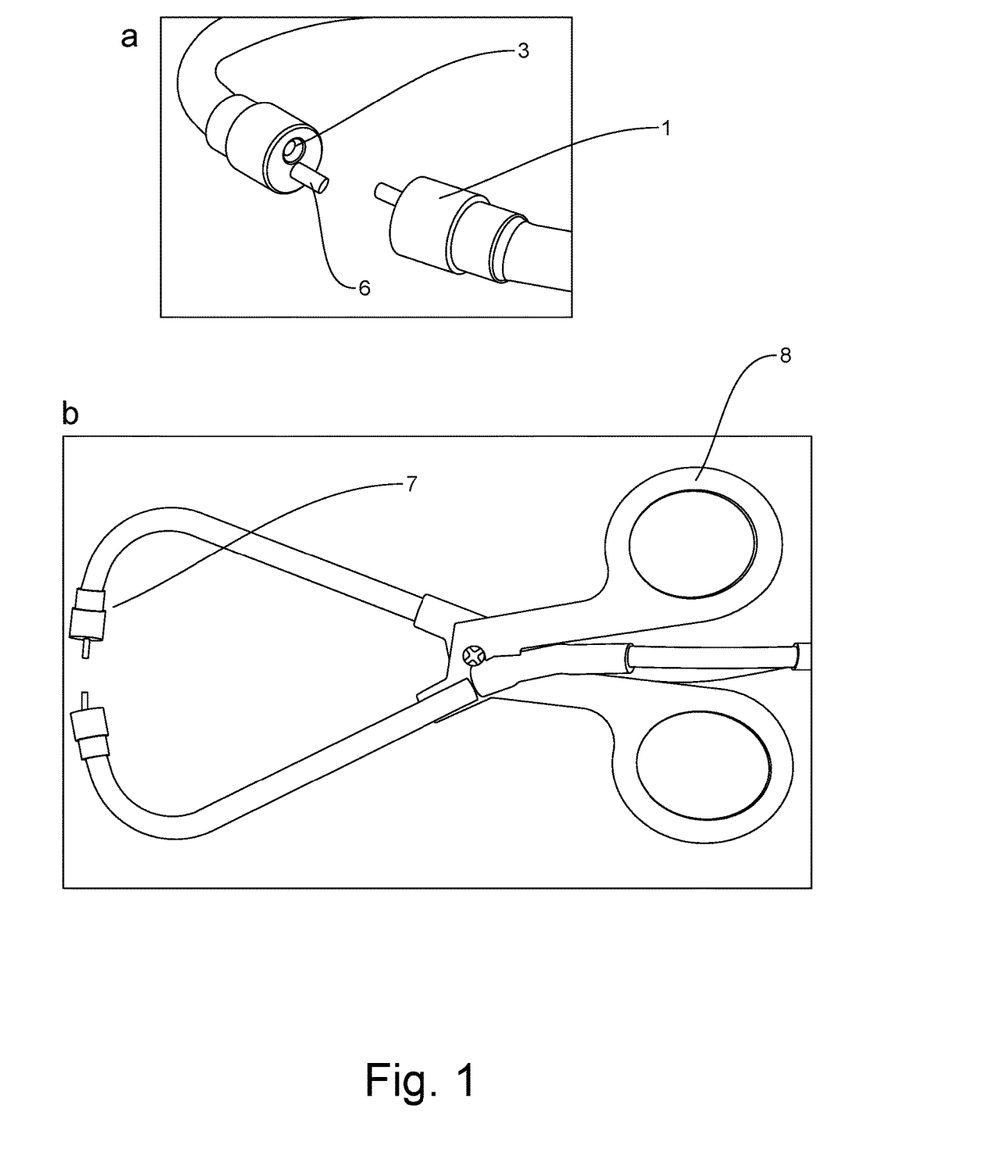
FIG. 1a is an enlarged view illustrating protruding sections 6 and clamping sections 1 of a tissue suturing device according to the present invention. The clamping section 1 being a base-like object has a cavity 3 for insertion of the protruding section 6 thereinto. When fragmentary portions of tissues to be sutured are pinched to apply pressure thereto, the protruding section 6 pushes the tissues into the clamping section 1.
FIG. 1b is a view illustrating a prototype of a tissue suturing device having a shape of scissor tongs according to the present invention. When fragmentary portions of tissues to be sutured are pinched and grips 8 are grasped, the protruding section 6 pushes the tissues into the clamping section 1.

FIG. 1 illustrate a prototype of the tissue suturing device according to the present invention. The tissue suturing device according to the present invention has a feature in the form of the protruding section 6 having a long diameter and the form of the clamping section 1. With those forms, it is possible to perform suturing treatment for tissues or the like, which is an effect unachievable in the related art.

The tissue suturing device according to the present invention at least includes the protruding sections 6 having a long diameter and including the central conductor 2 and/or the external conductor 9 for applying microwaves.

The protruding sections 6 having a long diameter are fixed to the respective clamping sections 1 being a base-like object, and it is preferred that the pair of protruding sections 6 having a long diameter be held in a state of being opposed to each other. As a matter of course, if desired, the protruding sections 6 having a long diameter need not be provided in pairs, and in addition, a plurality of protruding sections 6 having a long diameter may be provided so as to be paired with a plurality of corresponding protruding sections 6, or the protruding sections 6 may each have a comb-like shape or a planar shape.

When the protruding sections 6 having a long diameter are to be opposed to each other, the protruding sections 6 having a long diameter are opposed to each other with a clearance adaptable to a thickness of target tissues or the like so as to pinch the tissues or the like.

The clamping section 1 being a base-like object serves as a receptacle for the protruding section 6 having a long diameter on the mating side. The clamping section 1 may have a flat surface, but it is preferred that the clamping section 1 have the cavity 3 serving as a receptacle. It is preferred that the cavity 3 conform to the shape of the protruding section 6. When the protruding sections 6 are provided in pairs, the cavities 3 are similarly provided in pairs.

It is preferred that the tissue suturing device according to the present invention have a shape of scissor tongs and a structure of a sealing device. For example, the clamping sections 1 are fixed to respective distal end 7 of the scissor tongs, and when grips 8 of the scissor tongs are grasped, the fragmentary portions of the tissues to be sutured are brought into contact or overlap with each other by the opposing protruding sections 6, clamping sections 1, and/or cavities 3 of the clamping sections. Further, the contact or overlap portions are coagulated and/or fixed with microwaves, and thus the tissues to be sutured can be sutured (see FIG. 1b).

More specifically, the clamping sections 1 being a base-like object have a function of pinching (grabbing) the fragmentary portions of the tissues to be sutured through a grabbing or clamping action of the scissor tongs. Further, the shape of the scissor tongs may be a shape of slidable tongs (see WO 2008/056732).

The protruding section 6 as exemplified herein has a tapered tip end (see FIG. 5a) or a flat tip end with a circular or rectangular column. In this case, the central conductor 2 for transmitting microwaves is exposed from an insulating material at the tapered tip end portion or the tip end portion with a circular or rectangular column.

Note that, the present invention more preferably has a feature in that the diameter of each of the protruding section, the central conductor 2, and/or the external conductor 9 is decreased gradually or stepwise toward the tip end thereof. The inventors of the present invention has confirmed that such a tapered protruding section 6 (tapered structure) is capable of efficiently applying microwaves to the tissues to be coagulated, and further, suppressing damage to tissues to be prevented from being coagulated.

Figure 5:
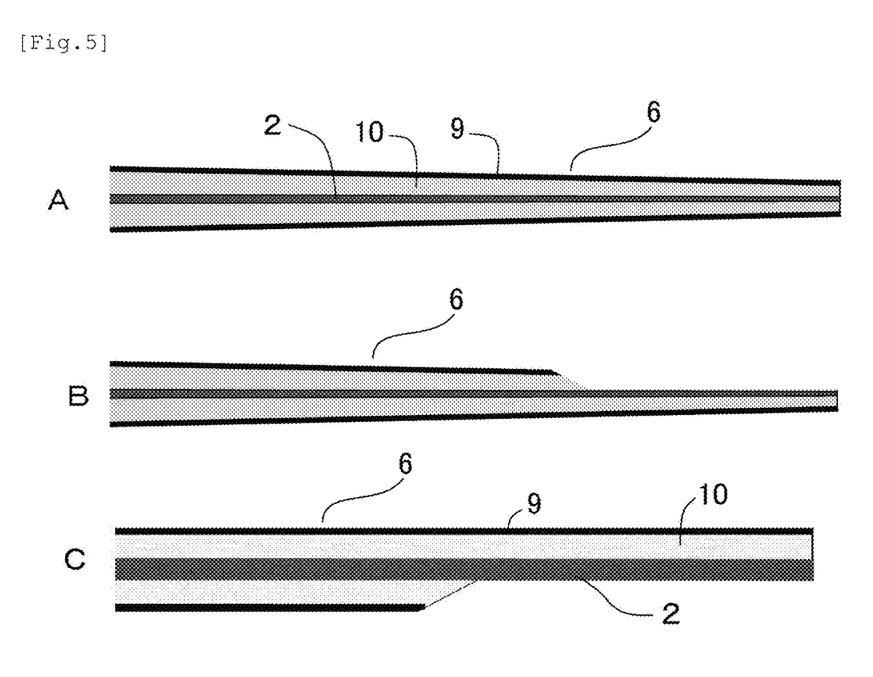
FIG. 5a is a view illustrating a protruding section 6 having a tapered tip end.
FIG. 5b is a view illustrating a protruding section 6 having a tapered tip end and a halved structure.
FIG. 5c is a view illustrating a protruding section 6 having a halved structure.

Further, the protruding section having a long diameter not only has the shape of the so-called circular or rectangular column, but may also have a halved structure (the structure refers to a half of a column cut into halves in the vicinity of the center along its longitudinal direction, in which the central conductor 2 for transmitting microwaves extends through the center of the column and is exposed when the column is cut into halves: the structure is obtained by cutting, in the longitudinal direction, a coaxial structure having an insulating layer formed between the central conductor 2 and the external conductor 9, thereby attaining a halved shape with the central conductor 2 exposed into a longitudinally elongated shape: see FIG. 5c). A part of the central conductor 2 is exposed in the longitudinal direction from the insulating material.

The inventors of the present invention has confirmed that such a protruding section 6 having the halved structure is capable of applying microwaves to the tissues to be coagulated, and further, suppressing damage to the tissues to be prevented from being coagulated.

The receiver of the microwaves to be applied from the central conductor 2 may be an opposing external conductor 9 on the mating side (for example, the clamping section 1 or the protruding section 6). The position of the external conductor 9 is adjusted depending on the purpose of suturing the tissues. For example, the clamping section 1 itself being a base-like object is formed of an insulator, and the external conductor 9 is arranged so as to surround a part of the clamping section being a base-like object, for example, an outer side of the clamping section.

In the case where the protruding section 6 having a long diameter has the halved structure, one opposing protruding section 6 having a long diameter may be formed into a halved shape, and the external conductor 9 may be arranged at the center of the halved column of another opposing protruding section 6 having a long diameter in such a form that the shape of the another protruding section 6 having a long diameter conforms to the halved shape of the one protruding section 6 having a long diameter. Alternatively, the central conductor 2 may be arranged at the center of the protruding section 6 itself having a long diameter and surrounded by an insulating material, and apart or all of an outer shape side of the insulating material may be surrounded by the external conductor 9.

A preferred protruding section 6 having a long diameter, a preferred clamping section 1 being a base-like object, and a preferred arm section are as follows.

The protruding section 6 having a long diameter has a circular, elliptical, semicircular, or halved shape in cross section. The length of the protruding section 6 having a long diameter as exemplified herein is 0.1 to 60 mm, preferably 0.5 to 10 mm, further preferably 1 to 5 mm, specifically, for example, 1.0 to 3.0 mm or about 2.0 mm. The diameter of the protruding section 6 as exemplified herein is 0.1 to 5 mm, preferably 0.2 to 3 mm, further preferably 0.5 to 2 mm, specifically, for example, 0.8 to 1.8 mm or 1.0 mm.

The clamping section 1 being a base-like object has a circular or rectangular shape. In a case where a single protrusion is provided, the maximum diameter of the clamping section 1 as exemplified herein is 1 to 10 mm, preferably 2 to 8 mm, further preferably 2.5 to 5 mm, more specifically, for example, 2.5 to 4 mm or 3 mm.

It is preferred that the clamping section 1 being a base-like object have the cavity 3 formed therein as a receptacle for the protruding section 6 having a long diameter. It is only necessary that the cavity 3 have a shape and length conforming to the shape of the protruding section 6 having a long diameter. The maximum diameter of the cavity 3 as exemplified herein is 0.3 to 8 mm, preferably 0.4 to 5 mm, further preferably 0.8 to 4 mm, specifically, for example, 0.9 to 3.0 mm or 1.5 mm.

The cavity 3 has a shape conforming to the shape of the protruding section 6 having a long diameter, and the maximum depth of the cavity 3 varies depending on tissues to be pinched. In general, the maximum depth as exemplified herein is 0.5 to 5 mm, preferably 1.0 to 3 mm, further preferably 1.5 to 2.5 mm, specifically, for example, 1.8 to 2.3 mm or 2.0 mm.

The clamping section being a base-like object is connected to the arm section, and the central conductor 2 for transmitting microwaves extends therethrough. The diameter of the arm section is not particularly limited, but the tissues are pinched by the pinching mechanism including the opposing protruding sections having a long diameter and/or the opposing clamping sections being a base-like object, and hence a material, thickness, and length capable of maintaining corresponding strength are adjustable by an obvious method itself. For example, in a case where stainless steel is selected as the material, the diameter of the arm section is about 3 to 6 mm.

The tissue suturing device according to the present invention is connected to a microwave generator through a microwave transmitting section including a coaxial cable.

In the present invention, the central conductor 2 and the external conductor 9 are prepared by using a so-called electrical conductor. Further, it is preferred that the conductor be made of a non-magnetic material. Specific examples of the non-magnetic material include brass (copper+tin), phosphor bronze (copper+tin+phosphorus), copper, zinc, gold, and silver alloy. The insulator is not particularly limited as long as the insulator is a so-called heat-resistant substance having property of being less liable to transfer electricity or heat. The heat-resistant temperature is not particularly limited as long as the temperature is substantially equal to or higher than 120° C.

In a case of a stationary oscillator, the coaxial cable connecting the power source and the central conductor 2 is the microwave transmitting section, which may be a tubular, flexible, and bendable cable (tube for covering the coaxial cable). In a case of a portable oscillator, an electrical cord is provided.

In the tissue suturing device according to the present invention, the central conductor 2 applies microwaves from the power source through the coaxial cable to the biological tissues to be sutured or the like. In the present invention, the voltage to be applied is preferably 1 V to 60 V. When the voltage is higher than 60 V, damage to the tissues may become serious. Further, the voltage lower than 15 V is a condition that is necessary also in consideration of a case of performing microvascular hemostasis or avoiding thermal damage to a neighboring region (cerebral surgery).

FIG. 1 are photographs of a main body of the tissue suturing device according to the present invention. The protruding section 6 having a long diameter is correspondingly insertable into the cavity 3 of the opposing clamping section 1 being a base-like object. The protruding section 6 having a long diameter includes the central conductor 2 for transmitting microwaves, and the external conductor 9 is wrapped around an outer circumference of the clamping section 1 being a base-like object (the clamping section 1 includes the external conductor 9). When the grips 8 are grasped in a similar manner to that of the scissor tong tongs, both the protruding sections 6 having a long diameter are inserted into the corresponding cavities 3.

FIGS. 2A to 2D are views illustrating the tissue suturing device according to the present invention.

Figure 2A:
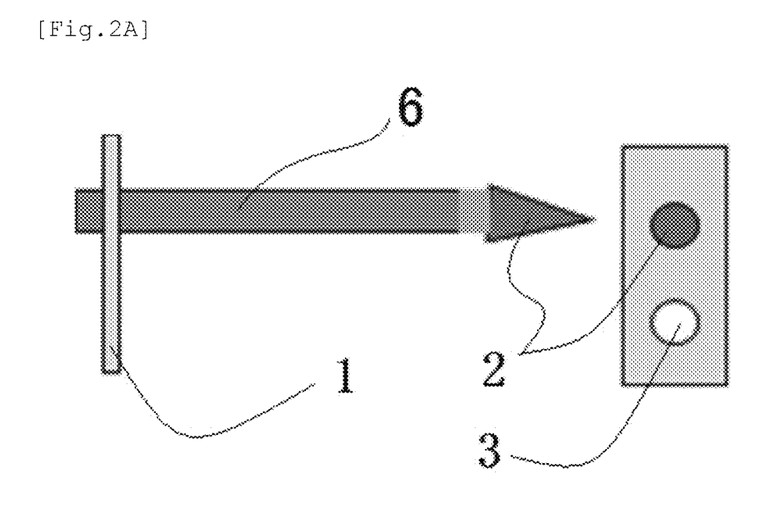
FIG. 2A is a view illustrating an example of the clamping section 1 being a base-like object and the protruding section 6 of the tissue suturing device according to the present invention.

FIG. 2A illustrates a relationship among the clamping section 1 being a base-like object, the central conductor 2 for transmitting microwaves, and the cavity 3.

Figure 2B:
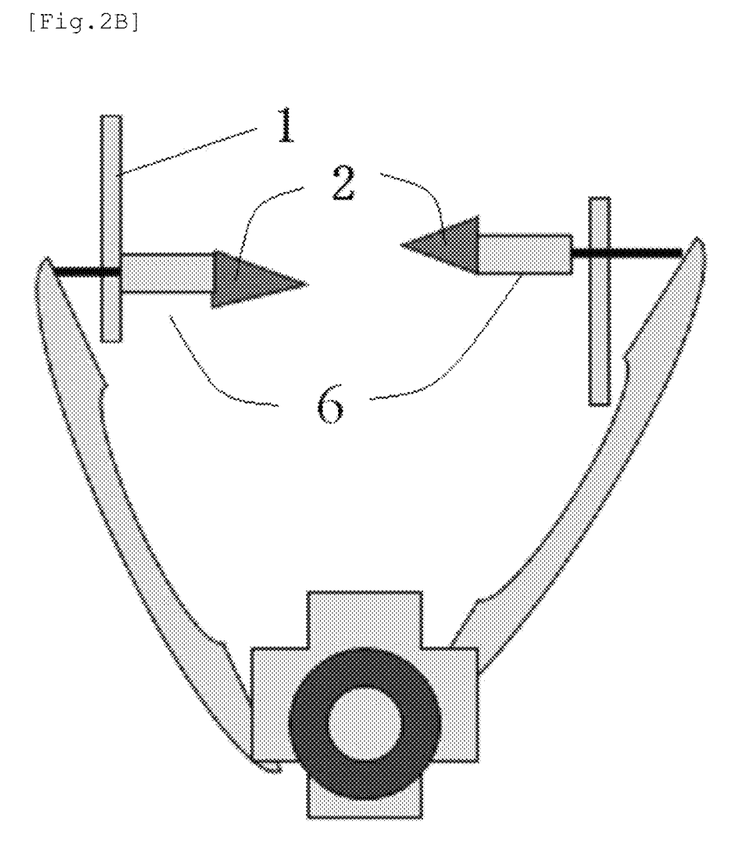
FIG. 2B is a view illustrating an example of the entire tissue suturing device according to the present invention.

FIG. 2B illustrates that, when the protruding sections 6 having a long diameter in the tissue suturing device according to the present invention are provided in pairs, the protruding sections 6 having a long diameter are arranged with a slight shift therebetween so that both the protruding sections 6 having a long diameter can reach the clamping sections 1 being a base-like object into contact therewith.

Figure 2C:
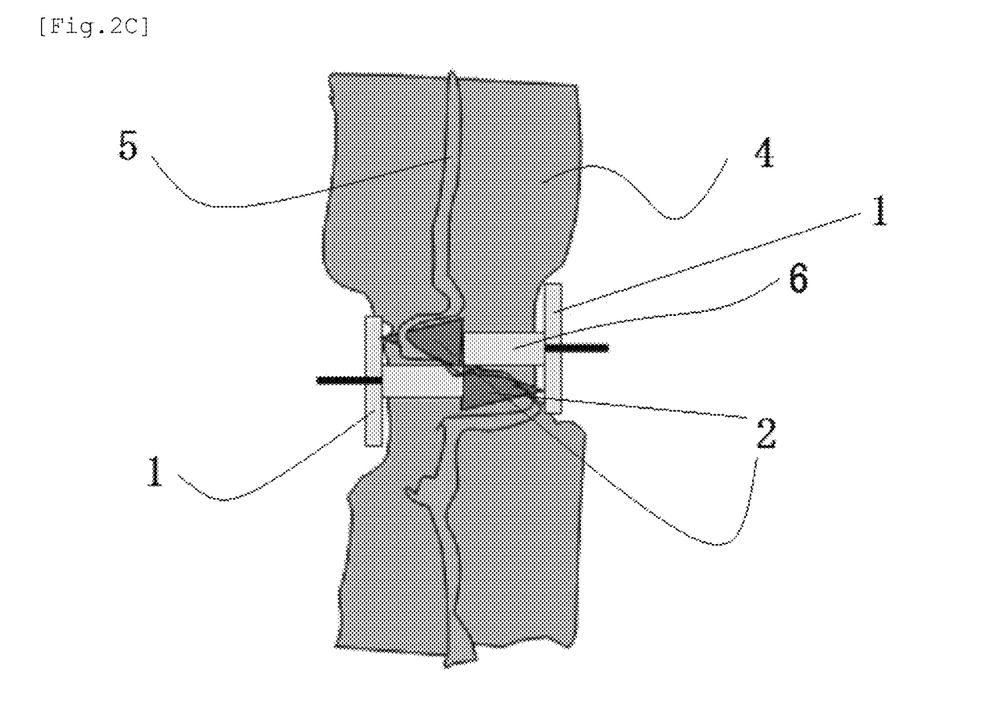

FIG. 2C illustrates a state in which tissues 4 are pinched and sutured. FIG. 2C illustrates a contact relationship among the tissues 4, a gap 5 between tissues, the opposing protruding sections 6 having a long diameter, and the opposing clamping sections 1 being a base-like object. More specifically, the two protruding sections 6 having a long diameter push the tissues 4 into the opposite sides so as to compress, coagulate, and fix the tissues 4.

Figure 2D:
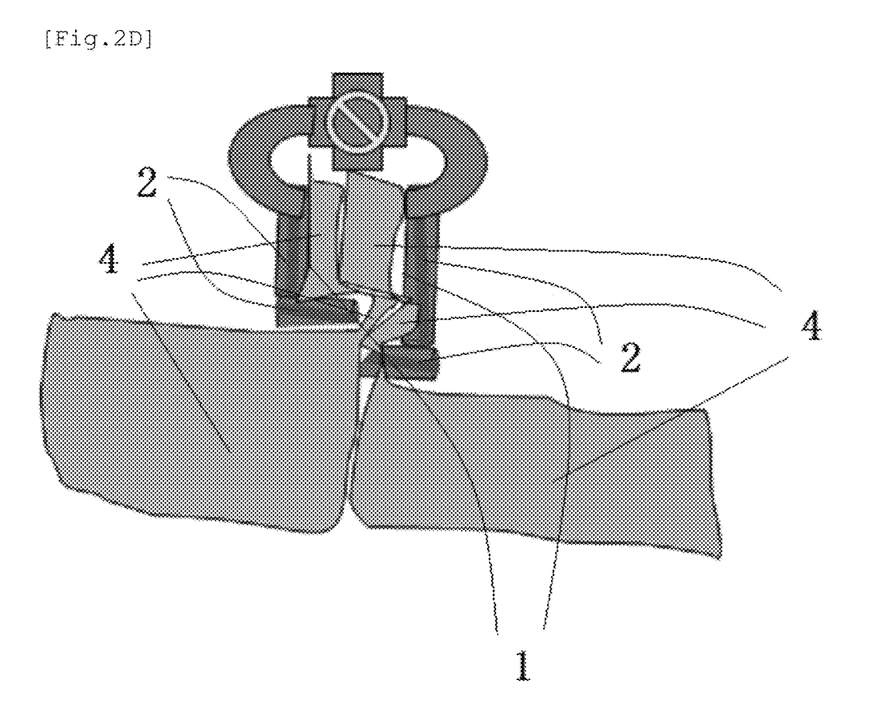

FIG. 2D illustrates another shape of the tissue suturing device according to the present invention. In this shape, the protruding sections 6 having a long diameter are opposed to each other, but are not brought into contact with the clamping section 1 being a base-like object. In FIG. 2D, the two protruding sections 6 having a long diameter pinch the tissues 4 therebetween so as to compress, coagulate, and fix the tissues 4.

Figure 3:
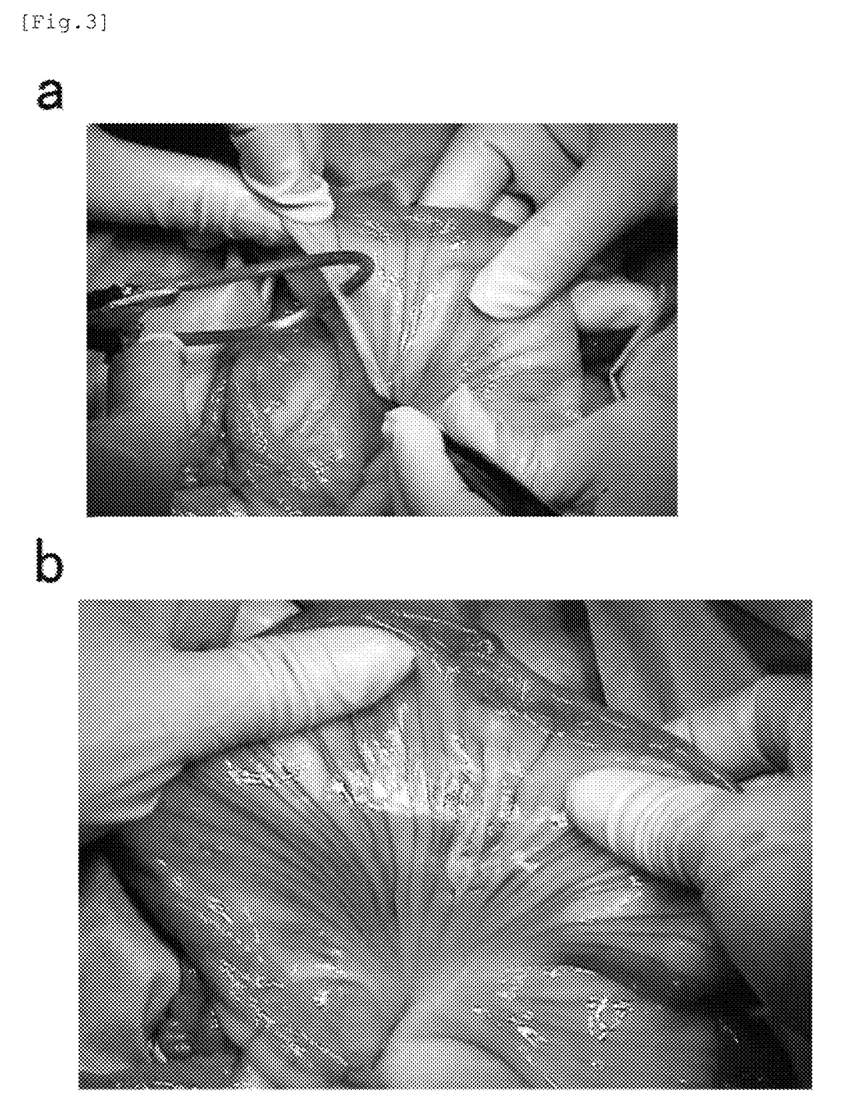
FIG. 3 are views illustrating an example of use of the tissue suturing device according to the present invention in an experiment of closing an incision of pig mesentery.
Figure 4:
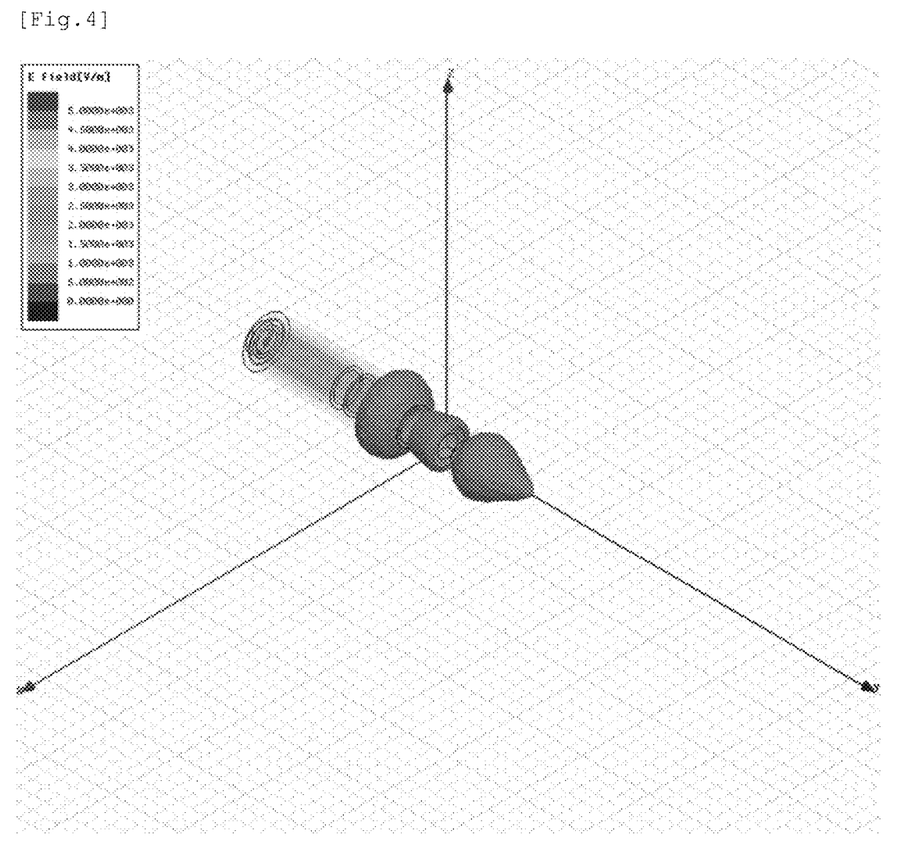
FIG. 4 is a view illustrating an E-field (V/m) generated through irradiation of microwaves in the tissue suturing device according to the present invention in a case where a needle-like (the diameter of a central conductor 2 is decreased gradually or stepwise toward the tip end thereof.

In FIG. 3a, it was confirmed that, after pig mesentery was cut away, the protruding sections 6 and the clamping sections 1 of the tissue suturing device according to the present invention grabbed stumps (tissue edges) of the pig mesentery, and the stumps were clamped and microwaves were applied thereto so that the mesentery was able to be closed due to the same effect as that of the suturing.

In FIG. 3b, tension is applied to the line after the closing operation so as to confirm the fixation of suturing. Although the experiment was directed to the closure of an incision of the pig mesentery, the suturing was completed several times as quick as the case of stitching with a surgical stitch according to the related art, and the stability of the resultant sutured region was significantly excellent. Besides, there was no need to remove the surgical stitch after the surgical operation, and hence it was possible to realize a surgical operation with no foreign matter remaining in the body. Thus, it was confirmed that the tissue suturing device was significantly excellent.

In use, an output connector and the tissue suturing device according to the present invention were connected to each other. Then, the protruding sections 6 having along diameter were brought into contact with regions of the target tissues 4 to be sutured so as to pinch the regions, and microwaves were applied thereto. Then, the target tissues were coagulated and fixed substantially up to a depth of 1.5 mm, to thereby stitch the tissues.

INDUSTRIAL APPLICABILITY

As described above, in the domain of surgical treatment of the medical field, the tissue suturing device according to the present invention can achieve suturing in a wide range of biological tissues or the like to be sutured through application of microwaves to the biological tissues. In particular, the tissue suturing device is applicable to suturing of a ligament, an intestinal tract, a blood vessel, and the like. Thus, the tissue suturing device according to the present invention is a surgical instrument that is highly operable to achieve tissue suturing easily. Further, the tissue suturing device does not generate any mist or smoke, and is significantly excellent in the ability of hemostasis. Thus, the tissue suturing device is also suitable as a surgical instrument to be used in a limited space.

REFERENCE SIGNS LIST

1: clamping section
2: central conductor
3: small hole/cavity or indentation
4: tissue
5: gap
6: protruding section or protuberance
7: cutting edge/distal end of scissor tong
8: grip
9: external conductor
10: insulator

The invention claimed is:

1. A tissue suturing device, comprising:
a clamping section comprising two or more opposing clamping elements; and
each of said opposing clamping element comprising a planar surface (1), wherein said planar surface (1) comprises:
a protuberance (6) comprising a central conductor and/or an external conductor configured to transmit a microwave, and
a recessed area (3) configured to accept said protuberance (6) on said opposing clamping element
such that said protuberance (6) and said recessed area (3) on the planar surface (1) of said opposing clamping element push different portions of tissues into said recessed area with a shift therebetween under pressure to bring different portions of the tissues to be sutured into contact or overlap with each other, and wherein said protuberances (6) are configured to apply microwave to the tissues thereby suturing the different portions of tissues together in a non-contiguous manner.

2. The tissue suturing device according to claim 1, wherein said tissue suturing device is scissor tong-shaped.

3. The tissue suturing device according to claim 1, wherein each of said planar surface (1) comprises two or more protuberances (6) formed in an array, and two or more corresponding recessed areas (3) formed in an array so as to serve as corresponding receptacles for the opposing protuberances in the array.

4. The tissue suturing device according to claim 3, wherein the array comprises a plurality of arrays.

5. The tissue suturing device according to claim 1, wherein said protuberances (6) comprise a cylindrical section, and wherein said recessed areas have a structure to serve as receptacles for said cylindrical section of said protuberances (6).

6. The tissue suturing device according to claim 1, wherein said protuberance (6) comprises the central conductor, and wherein said clamping section comprises the external conductor.

7. The tissue suturing device according to claim 1, wherein said protuberances (6) and said recessed areas (3) comprise two sets of protuberances (6) and recessed areas (3) that are opposite of each other, wherein one of said protuberance (6) comprises the central conductor and the other said protuberance (6) comprises the external conductor.

8. The tissue suturing device according to claim 7, wherein said microwave is propagated from said central conductor of one protuberance (6) toward the external conductor of said opposite protuberance (6).

9. The tissue suturing device according to claim 1, wherein a diameter of said protuberance (6), the central conductor, and/or the external conductor is decreased gradually or stepwise toward a tip end thereof.

10. The tissue suturing device according to claim 1, wherein said protuberance (6) has a halved structure.

11. A method for suturing together two different tissue portions, said method comprising:
contacting a first tissue portion to a second tissue portion using said clamping section of a tissue suturing device of claim 1; and
transmitting microwave through said conductor to a contacted area of said first and said second tissue portions under conditions sufficient to cause said first and said second tissue portions to be sutured together in a non-contiguous manner.

12. The method of claim 11, wherein said transmitted microwave also coagulates at least a portion of said contacted area of said first and said second tissue portions.

* * * * *